United States Patent

Vanlerberghe et al.

[11] Patent Number: 4,668,509
[45] Date of Patent: May 26, 1987

[54] POLYTHIOALKANECARBOXYLIC ANIONIC PRODUCTS, THEUR USE AND PREPARATION

[75] Inventors: Guy Vanlerberghe, Souilly; Henri Sebag, Paris, both of France

[73] Assignee: L'Oreal, Paris, France

[21] Appl. No.: 637,023

[22] Filed: Aug. 2, 1984

[30] Foreign Application Priority Data

Aug. 2, 1983 [LU] Luxembourg .............................. 84943

[51] Int. Cl.[4] ...................... A61K 7/09; C07C 149/273
[52] U.S. Cl. ......................... 424/72; 562/426; 562/429; 260/501.15; 424/47; 424/59; 424/71; 132/7; 8/405; 514/571
[58] Field of Search .............................. 562/429, 426; 260/501.15; 424/72, 71, 59, 45, 47; 8/405; 132/7; 514/571

[56] References Cited

FOREIGN PATENT DOCUMENTS 2080303 2/1982 United Kingdom ................ 562/426
2114988 9/1983 United Kingdom .................. 424/72

*Primary Examiner*—Natalie Trousof
*Assistant Examiner*—Bruce D. Gray
*Attorney, Agent, or Firm*—Cushman, Darby & Cushman

[57] ABSTRACT

Polythioalkanecarboxylic products of formula:

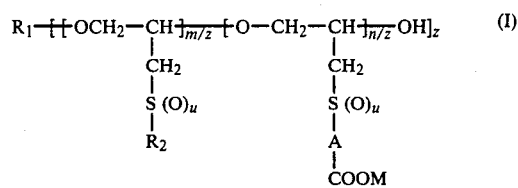

in which $R_1 = C_{6\text{-}30}$ aromatic or alkylaromatic radical; $R_2 = C_4\text{-}C_{18}$ alkyl; $A = C_{1\text{-}3}$ alkylene; $M = H$, alkali metal or alkaline earth metal, an ammonium ion or a substituted ammonium ion; $z = 1\text{-}6$; $m = 1\text{-}10$; $n = 1\text{-}20$; and $u = $ zero or 1 are disclosed.

A process of preparation comprising, in a first stage, reacting an alcohol or phenol of formula $R_1(OH)_z$ (II) with an epihalogenohydrin of formula

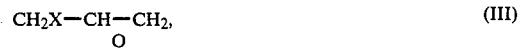

in which $X = Cl$ or $Br$, in the presence of a Lewis acid, to give the intermediates of the formula:

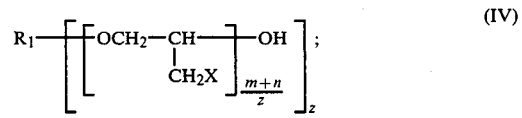

and in a second stage, the two compounds of formulae $R_2SH$ (V) and HS—A—COOH (VI), in which $R_2$ and A have the meanings indicated above, are reacted simultaneously or successively with the compound of the formula (IV) is also disclosed.

The compounds of the formula (I) are used in cosmetic compositions.

8 Claims, No Drawings

POLYTHIOALKANECARBOXYLIC ANIONIC PRODUCTS, THEIR USE AND PREPARATION

This invention relates to polythioalkanecarboxylic anionic products containing at least one alkylthio group, compositions containing them and a process for their preparation.

French Patent Application No. 2,442,869 describes various products prepared from alcohols, 1,2-diols or 1,3-diols, especially polythioalkanecarboxylic anionic oligomers which can optionally contain alkylthio groups. The preparation of these products involves the polyaddition of alkyl glycidyl thioethers and epichlorohydrin, followed by substitution of the chlorine atoms by reaction with mercaptocarboxylic acid esters.

This process has several economic and practical disadvantages. Alkyl glycidyl thioethers are expensive and not readily available in industrial quantities. Mercaptocarboxylic acid esters are malodorous and are difficult to handle.

Moreover, the process described recommends the use of basic catalysts with the alkyl glycidyl thioethers; this is not possible with epichlorohydrin. Under acid catalysis, the polymerization of the alkyl glycidyl thioethers cannot be carried out with boron trifluoride, and with tin tetrachloride substantially larger quantities are necessary than for a polyaddition of epichlorohydrin by itself. The use of the products prepared by this process for cosmetic or pharmaceutical applications therefore involves separation of the tin derivatives by difficult and expensive purification treatments.

This invention provides products comprising a compound of formula (I):

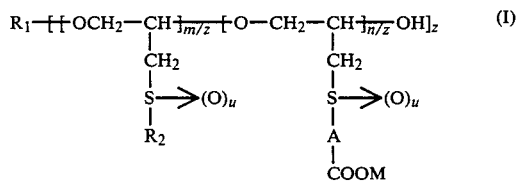

in which
- $R_1$ denotes an aromatic or alkylaromatic radical of 6 to 18 carbon atoms and is preferably derived by removing the —OH hydrogen atom from a monohydric or polyhydric phenol radical derived from benzene, naphthalene, biphenyl, diphenylmethane or 2,2-diphenylpropane, which is unsubstituted or substituted by one or more alkyl radicals of 1 to 12 carbon atoms, or an aromaticoxyethyl, alkylaromaticoxyethyl, aromatic polyoxyethyl or alkylaromaticpolyoxyethyl radical, of valency z, the alkyl part having from 1 to 12 carbon atoms and the oxyethyl part containing from 1 to 20 ethylene oxide groups;
- z denotes an integer from 1 to 6;
- m denotes an integer or decimal number from 1 to 10;
- n denotes an integer or decimal number from 1 to 20;
- u denotes zero or 1;
- $R_2$ denotes an aliphatic radical, preferably an alkyl radical, of 4 to 8 carbon atoms;
- A denotes an alkylene radical of 1 to 3 carbon atoms; and
- M denotes a hydrogen atom, an alkali metal or alkaline earth metal atom, an ammonium ion or a substituted ammonium ion, preferably corresponding to triethanolamine, triisopropanolamine, 2-amino-2-methylpropan-1-ol or 2-amino-2-methylpropane-1,3-diol.

It should be understood that in formula (I) the units corresponding to the chain or chains may be present in any order and the units will generally form rather statistical oligomers than block oligomers.

These products may be made by, in a first stage, telomerizing an epihalogenohydrin with an alcohol or phenol, in the presence of a small quantity of a Lewis acid, preferably $BF_3$ or $SnCl_4$, as a catalyst, and, in a second stage, reacting the product obtained in the first stage with an alkylmercaptan (which is easier to obtain in industrial quantities and is cheaper than alkyl glycidyl thioethers) and a mercaptocarboxylic acid (which is more readily available than its esters and has a less unpleasant odour).

The expression "telomerizing" denotes the reaction of an epoxide with a compound possessing an active hydrogen atom. The compound possessing the active hydrogen is called a telogen, the epoxide compound is called a taxogen and the reaction product is called a telomer.

More specifically, this process comprises, in a first stage, telomerizing an epihalogenohydrin of formula (II):

in which X denotes Cl or Br, with an alcohol or phenol of formula (III):

in which $R_1$ denotes an aliphatic, cycloaliphatic, aromatic or alkylaromatic radical of valency z, which has from 1 to 30 carbon atoms and can be interrupted by one or more oxygen atoms, and Z denotes an integer from 1 to 6, in the presence of a Lewis acid, preferably $BF_3$ or $SnCl_4$ and, optionally in the presence of a solvent, preferably a hydrocarbon or chlorohydrocarbon solvent, such as hexane, heptane, benzene, toluene, methylene chloride or dichloroethane, preferably at a temperature of from 30° to 100° C. and more preferably of from 50° to 75° C., to give an intermediate product of formula (IV):

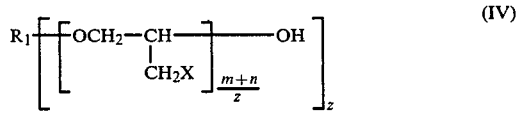

in which $R_1$, X, n, m and z have the meanings indicated above, and, in a second stage, reacting the intermediate of formula (IV) with an alkylmercaptan of formula (V):

and with a mercaptocarboxylic acid of formula (VI):

the compounds of formulae (V) and (VI) being added either successively or simultaneously, in the presence of an alkali metal methylate, ethylate, or hydroxide, preferably sodium or potassium methylate, ethylate or hydroxide, and a solvent, preferably an alkanol of 1 to 4 carbon atoms, an ether of a $C_{1-4}$ alkanol with ethylene glycol or diethylene glycol, or water, preferably at a temperature of from 80° to 120° C.

In formula (V), $R_2$ denotes an aliphatic radical, preferably an alkyl radical, of 4 to 18 carbon atoms.

In formula (VI), A denotes an alkylene radical of 1 to 3 carbon atoms.

The products obtained are optionally washed, preferably with hot water in an acid medium and then neutralized, if necessary, with an alkali metal hydroxide or alkaline earth metal hydroxide, aqueous ammonia or an amine, preferably hydroxylated amine.

The thioethers obtained can be converted to sulphoxides by oxidation, preferably in aqueous or aqueous-alcoholic solution, with hydrogen peroxide, more preferably 35% (130 volume) hydrogen peroxide, or a peracid, at a temperature of from 25° to 50° C.

It will be appreciated that this second step will generally result in a statistical mixture of compounds differing in the individual values of m/z and n/z.

Thus m/z and n/z correspond to statistical values dependent on the number of moles of alkylmercaptans and mercaptocarboxylic acids employed.

The quantity of catalyst to be used in the first stage is generally from 0.2 to 1% by weight, relative to the total weight of the reaction mixture. In the second stage, a stoichiometric quantity or a slight excess of alkali metal methylate, ethylate or hydroxide is generally used.

Examples of compounds of the formula (III) are:

aliphatic monoalcohols and polyalcohols of 1 to 22 carbon atoms; α-diols, α,ω-diols, glycerol and sorbitol are preferred among the polyols;

polyethoxylated glycols having 1 to 20 ethylene oxide groups, and alkyl ethers, the alkyl group having 1 to 18 carbon atoms, of ethylene glycol or a polyethoxylated glycol containing from 2 to 20 ethylene oxide groups;

cycloaliphatic alcohols, such as cyclohexanol; sterols;

monohydric and polyhydric phenols derived from benzene, naphthalene, biphenyl, diphenylmethane and 2,2-diphenylpropane, which are unsubstituted or substituted by one or more alkyl groups of 1 to 12 carbon atoms, and which contain a total of 6 to 18 carbon atoms; and aryl ethers and alkylaryl ethers of glycol and of polyethyoxylated glycols, the polyethoxylated part having 2 to 20 ethylene oxide groups.

Linear alkylmercaptans having from 4 to 18 carbon atoms are preferred for compounds of formula (V). Mercaptoacetic acid and 2-mercaptopropanoic and 3-mercaptopropanoic acids are preferred for compounds (VI).

This invention also provides compositions containing at least one compound of formula (I) and a carrier.

The compounds of the formula (I) are advantageously used in cosmetic compositions and more particularly in hair treatment compositions, such as shampoos, rinse-off or leave-on after-shampoo products, products for more or less permanent shaping of the hair, and colouring products, as additives for improving the wetting, foaming, dispersing, emulsifying or solubilizing properties of the compositions.

They are also advantageously used in aqueous solutions, by themselves or in association with other compounds, for rinsing the hair, for example after the application of cationic products.

Depending on the application, the compounds of formula (I) can be used at a concentration of, say, 0.3 to 80% by weight of A.I. (active ingredient) and preferably of 0.5 to 30% of the total weight of the composition. The compositions containing the compound of formula (I) can be aqueous or aqueous-alcoholic solutions or dispersions, pastes, gels, creams, emulsions or solids or can be presented in aerosol form. The aqueous-alcoholic compositions preferably contain from 5 to 70% by weight of an alkanol of 1 to 6 and advantageously from 1 to 4 carbon atoms. Ethanol and isopropanol are preferred.

The compounds of formula (I) can be used by themselves, in particular for rinsing the hair, but they are normally used in association with other constituents, such as anionic, cationic, zwitterionic, amphoteric or non-ionic surface-active agents, anionic, cationic, zwitterionic or non-ionic polymers, proteins, foam synergistic agents, thickeners, opacifiers, super-fatting agents, preservatives, pigments, dyestuffs, sun filters, reducing or oxidizing agents, solvents, propellants such as "Freons", electrolytes or other adjuvants normally used in cosmetics.

The compositions of the invention preferably contain at least one compound of formula (I) and a cationic polymer and/or a non-ionic or cationic surface-active agent.

The pH of these compositions is generally from 3 to 10.

The compounds of the formula (I) can improve the foaming and/or detergent properties of the compositions and the comb-out, styling or hold of the hair.

This invention also provides a hair treatment process, wherein a sufficient quantity of a composition containing at least one compound of formula (I) is applied to the hair and, if appropriate, the hair is rinsed.

This invention also provides a two-stage hair treatment process. In a first stage, a cationic composition (containing a surface-active agent and/or a cationic polymer) is applied to the damp hair and, after a few minutes of contact, a composition containing at least one compound of formula (I) is applied, after which the hair is rinsed and/or dried if appropriate.

EXAMPLE 1

Preparation of a product of formula (I) in which:

| $R_1$ denotes | 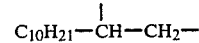 |
|---|---|
| $R_2$ denotes | $-C_8H_{17}$ |
| A denotes | $-CH_2-$ |
| M denotes | 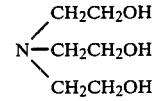 | m = 2
n = 8
z = 2
u = 0

(a)

Preparation of a mixture of polychlorinated compounds 0.21 ml of $BF_3$ etherate is added to 30.3 g of dodecane-1,2-diol (0.15 mol), and 138.7 g of epichlorohydrin (1.5 mol) are then added at 70° C. over a period of 1 hour 45 minutes. After about half the quantity of epichlorohydrin has been added, a further 0.21 ml of $BF_3$ is added. 30 Minutes after the addition of the epichlorohydrin has ended, there are no longer any detectable epoxide groups.

The mixture of polychlorinated compounds is in the form of a very viscous and very slightly coloured liquid.

(b)

Preparation of a mixture of compounds of the formula (I)

7.3 g of octylmercaptan (0.05 mol) are mixed with 18.7 g of thioglycolic acid (0.2 mol). 46 g (0.46 mol) of a 40% aqueous solution of NaOH are then introduced under a nitrogen atmosphere, followed, at 80° C., by 23 g of polychlorinated derivatives obtained according to (a) (0.25 equivalent of chlorine), solubilized in 40 g of butyldiglycol beforehand.

The reaction mixture is then heated at 100°–105° C. for 2 hours 30 minutes.

Part of the water is removed and heating is continued for 2 hours 30 minutes.

The reaction mixture is then taken up with 100 g of water and acidified by the adddition of 18 ml of concentrated hydrochloric acid.

The organic phase is separated off by decantation after the addition of about 30 g of dichloroethane, and then dried by heating under reduced pressure.

30 g of triethanolamine (0.2 mol) and 90 g of water are then added to give a solution containing about 50% of active ingredients, which is in the form of a pale yellow, opalescent liquid.

EXAMPLE 2

Preparation of a product of formula (I) in which:

| $R_1$ denotes | 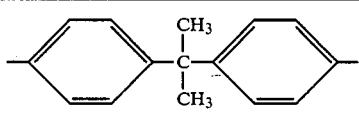 |
|---|---|
| $R_2$ denotes | $-C_{12}H_{25}$ |
| A denotes | $-CH_2-$ |
| M denotes | Na |

$m = 3$
$n = 12$
$z = 2$
$u = 0$ (a)

Preparation of a mixture of polychlorinated compounds 34.2 g of bisphenol A (0.15 mol) are dispersed in 35 g of dichloroethane at 50° C. 0.85 ml of $BF_3$ etherate is then added, followed, at about 60° C., by 208 g of epichlorohydrin (2.25 mol). The addition takes 1 hour 30 minutes. After heating for a further 1 hour, the solvent is evaporated off under reduced pressure.

(b)

Preparation of a mixture of compounds of the formula (I)

82 g of a 50% aqueous solution of NaOH are added, under a nitrogen atmosphere, to 37.4 g (0.4 mol) of thioglycolic acid, followed, at 80° C., by 53.8 g of polychlorinated compounds obtained according to (a). The addition takes 5 minutes. 30 g of methylcellosolve are added and the mixture is heated for 2 hours at 100°–105° C.

10 g of a 40% aqueous solution of NaOH are then added, followed, dropwise, by 20.2 g (0.1 mol) of dodecylmercaptan. Heating is then continued for 2 hours after the addition of 50 ml of water.

The reaction mixture is then acidified by the addition of 42 g of concentrated hydrochloric acid diluted in 300 ml of water.

The organic phase is separated off and washed again with 200 ml of water.

The product obtained is then taken up with 50 ml of 96° ethanol and 350 g of normal NaOH solution.

The ethanol is distilled at ordinary pressure and the solution is concentrated to 50% of active ingredients.

The solution thus obtained is in the form of a reddish-brown liquid.

EXAMPLE 3

Preparation of a product of formula (I) in which:

| $R_1$ denotes | 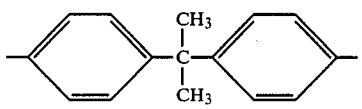 |
|---|---|
| $R_2$ denotes | $-C_8H_{17}$ |
| A denotes | $-CH-$<br>$\phantom{-}\vert$<br>$\phantom{-}CH_3$ |
| M denotes | Na |

$m = 3$
$n = 12$
$z = 2$
$u = 0$ 92 g of a 40% aqueous solution of NaOH are added, under a nitrogen atmosphere, to a mixture of 15 g of octylmercaptan (0.1 mol) and 44.6 g of 2-mercaptopropionic acid (0.4 mol), and 53.8 g of a mixture of polychlorinated compounds obtained in part (a) of Example 2 (0.5 equivalent of chlorine), diluted with 30 g of methylcellosolve (ethylene glycol monomethyl ether) beforehand, are then added at 80° C. over a period of 30 minutes.

The reaction mixture is heated for 10 hours at 100°–105° C. and is then diluted with 200 g of water and acidified by the addition of 40 g of concentrated hydrochloric acid.

The organic phase is separated off, washed again with 150 ml of hot water and then neutralized with 60 g of a 20% aqueous solution of NaOH.

The solution obtained is in the form of a very thick, brown liquid which gives opalescent solutions after dilution.

EXAMPLE 4

Preparation of a product of formula (I) in which:

| $R_1$ denotes | $-C_6H_{13}$ |
|---|---|
| $R_2$ denotes | $-C_4H_9$ |
| A denotes | $-CH_2-$ |

-continued

| M denotes | $\begin{array}{c} \phantom{N-}CH_2-CH_2OH \\ N-CH_2-CH_2OH \\ \phantom{N-}CH_2-CH_2OH \end{array}$ |
|---|---| m = 5
n = 15
z = 1
u = 0

(a)

Preparation of a mixture of polychlorinated compounds 185 g (2 mol) of epichlorohydrin are added to 10.2 g of hexanol (0.1 mol) at 50°–55° C., in the presence of 0.5 ml of SnCl$_4$, which is added in three portions. The addition of eopichlorohydrin takes 2 hours.

(b)

Preparation of a mixture of compounds of the formula (I)

60 g of a 40% aqueous solution of NaOH are added to 29 g of mercaptoacetic acid (0.3 mol), followed, at 80° C., by 39 g of polychlorinated compounds obtained according to (a), diluted with 40 g of methylcellosolve beforehand.

The addition takes 1 hour.

The reaction mixture is then heated for 1 hour at 90°–100° C.

10 g of a 40% aqueous solution of NaOH are then added, followed, dropwise at 80° C., by 9 g of butylmercaptan (0.1 mol).

After heating for 3 hours at 80°–90° C., the reaction medium is diluted with 100 ml of water and acidified by the addition of 13 ml of concentrated hydrochloric acid.

The organic phase is separated off after the addition of 100 ml of dichloroethane.

After evaporation of the solvent, 39 g of a product are obtained which is neutralized with 28 g of triethanolamine and diluted with 66 g of water to give a solution containing about 50% of active ingredients.

EXAMPLE 5

Preparation of a product of formula (I) in which:

$R_1 = $ [4-C$_9$H$_{19}$-phenyl]$-(CH_2-CH_2O)_4-$ $R_2 = -C_{18}H_{37}$
$A = -CH_2-$
$M = Na$ m = 2
n = 18
z = 1
u = 1

(a)

Preparation of a mixture of polychlorinated compounds 0.7 ml of BF$_3$ etherate is added to 39.6 g (0.1 mol) of nonylphenol polyethoxylated with 4 mol of ethylene oxide, and 185 g (2 mol) of epichlorohydrin are then added at 60° C. over a period of 2 hours. After about half the quantity of epichlorohydrin has been added, a further 0.32 ml of BF$_3$ etherate is added.

Stirring and heating at 60° C. are continued for about 15 minutes after the addition. The mixture of polychlorinated compounds is in the form of a very viscous, brown liquid.

(b)

Preparation of a mixture of compounds of the formula (I)

182.7 g of a 40% aqueous solution of NaOH are added, under a nitrogen atmosphere, to 84.11 g (0.9 mol) of thioglycolic acid, and 112.3 g of polychlorinated compounds obtained above, diluted with 55 g of methylcellosolve, are then added at 70° C. over a period of 20 minutes.

The reaction mixture is then heated at 95° C./100° C. for 2 hours. The extent of reaction, determined by analysis of the remaining sulphydryl groups and measurement of the alkalinity, is 93%.

At 80° C., 28.6 g of octadecylmercaptan (0.1 mol) are then added, followed by 10.3 g of a 40% aqueous solution of NaOH.

The reaction mixture is heated for 1 hour 30 minutes at 95° C.

The extent of reaction, determined by analysis of the remaining sulphydryl groups and measurement of the alkalinity, is about 95%.

The mixture is diluted with 300 ml of water and acidified with 200 g of 6N hydrochloric acid.

After heating for a few minutes at 70°/75° C., the organic phase is decanted and then washed with 400 ml of water.

The product obtained is then neutralized with 144 g of a 20% aqueous solution of NaOH.

The solution thus obtained is in the form of a milky solution.

7.2 ml of 200 volume hydrogen peroxide are added dropwise, at 30° C., to 60 g of the solution thus obtained (0.117 equivalent of basicity) to give a mixture of polysulphoxides.

EXAMPLE 6

Preparation of a product of formula (I) in which:

$R_1 = C_4H_9-O-CH_2-CH_2-$
$R_2 = -C_4H_9$
$A = -CH_2-CH_2-$
$M = Na$ m = 8
n = 4
z = 1
u = 0

(a)

Preparation of a mixture of polychlorinated compounds 0.8 ml of BF$_3$ etherate is added to 23.6 g of butoxyethanol (0.2 mol), and 222 g of epichlorohydrin (2.4 mol) are then added dropwise at 50° C.

The addition takes 2 hours 10 minutes.

The temperature is maintained and the stirring continued for 1 hour after the addition has ended.

(b)

Preparation of a mixture of polyanionic products 53.6 g of a 40% aqueous solution of NaOH (0.536 mol) are added to 27.6 g of 3-mercaptopropionic acid (0.26 mol). The reaction is exothermic. 79.8 g (0.78 equivalent of chlorine) of polychlorinated derivatives, previously dissolved in 40 g of methylcellosolve, are then added at 80° C.

The addition takes 1 hour 15 minutes.

The mixture is heated for a further 1 hour 30 minutes at 90° C.

The extent of reaction is 98%.

53.6 g of a 40% solution of NaOH and 46.9 g of butyl-mercaptan (0.52 mol) are added simultaneously to the reaction mixture obtained. The resulting mixture is diluted with 50 g of methylcellosolve and then heated at 90°–95° C. for 4 hours 30 minutes.

300 g of water at 90° C., and then 42 ml of 6N hydrochloric acid, are added to the reaction mixture obtained. The organic phase is then separated off.

80 ml of water and 12.8 g of a 40% solution of NaOH are added to 109 g of the product thus obtained (1.17 meq/g). This gives a dispersion containing 0.62 meq/g of basicity.

EXAMPLE 7

Preparation of a product of formula (I) in which:

| $R_1$ denotes | 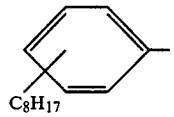 |
| --- | --- |
| | $C_8H_{17}$ |
| $R_2$ denotes | $-nC_8H_{17}$ |
| $A =$ | $-CH_2-CH_2-$ |
| $M =$ | Na |

$m = 5$
$n = 5$
$z = 1$
$u = 0$ 0.56 ml of $BF_3$ etherate is added to 41.2 g of octylphenol (0.2 mol), and 185 g of epichlorohydrin (2 mol) are then added dropwise at 60° C. over a period of 2 hours.

After the addition, a further 0.15 ml of catalyst is added and heating is continued for 1 hour.

45.1 g of 3-mercaptopropionic acid (0.425 mol) are neutralized, under nitrogen, with 98 g of a 40% solution of sodium hydroxide, and 96.4 g (0.85 equivalent of chlorine) of previously obtained polychlorinated compounds, diluted in 50 g of methylcellosolve, are then added at a temperature of 80° C.

The reaction mixture is then heated at 90° C. for 1 hour 45 minutes.

43.8 g of 40% NaOH solution (0.44 equivalent) and 62.2 g of octylmercaptan (0.425 mol) are then added simultaneously over a period of 35 minutes at a temperature of 75°–80° C.

Heating is continued for 5 hours at 90°–100° C.

The reaction mixture is diluted with 130 ml of water and acidified with 51 ml of hydrochloric acid.

The organic phase is separated off and washed with 190 ml of water at 90° C.

34.4 g of 40% NaOH solution, diluted with 90 ml of water, are added to 274 g of the product thus obtained, which has an acid value of 1.25 meq/g.

The dispersion thus obtained is evaporated to dryness.

After rinsing with acetone, the products is finally in the form of al light beige powder which dissolves in water to give a slight opalescence.

FORMULATION EXAMPLES

EXAMPLE $A_1$

A shampoo having the following composition is pepared:

| | |
| --- | --- |
| Mixture of compounds of Example 3 | 3.2 g |
| Sodium salt of sulphated alkanol($C_{12}$—$C_{14}$) ethoxylated with 2.2 mol of ethylene oxide, containing 25% of active ingredients | 36 g |
| Lauric diethanolamide | 1.8 g |
| NaOH q.s. pH = 7.4 | |
| Water q.s. | 100 g |

EXAMPLE $A_2$

A shampoo having the following composition is prepared:

| | |
| --- | --- |
| Mixture of compounds of Example 2 | 3 g |
| Non-ionic surface-active agent of the formula: R—CHOH—$CH_2$—O—($CH_2$CHOH$CH_2$O)$_n$—H in which R = mixture of $C_9$-$C_{12}$ alkyl radicals and n represents an average statistical value of about 3.5 | 10 g |
| NaOH q.s. pH 7 | |
| Water q.s. | 100 g |

The shampoos of Examples $A_1$ and $A_2$ rapidly develop a copious lather. After rinsing, the hair is soft and easy to comb out.

EXAMPLE $A_3$

The following rinse-off after-shampoo composition is prepared:

| | |
| --- | --- |
| Mixture of compounds of Example 3 | 2 g |
| Mixture of cetylstearyl alcohol and cetyl-stearyl alcohol ethoxylated with 15 mol of ethylene oxide, sold under the name SINNOWAX AO by HENKEL | 3 g |
| Hydroxyethylcellulose sold under the name CELLOSIZE QP 4400H by Union Carbide | 2 g |
| Distearyldimethylammonium chloride | |
| Quaternary polyvinylpyrrolidone copolymer having a molecular weight of 1,000,000, marketed under the name Gafquat 755 by General Aniline | 1 g |
| NaCl | 1 g |
| NaOH q.s. pH 7.7 | 2 g |
| Water q.s. | 100 g |

This composition is applied to clean damp hair. After an interval of about 10 minutes, the hair is rinsed.

The hair is easy to comb out. Styling is easy and the hair holds its shape for a long time.

EXAMPLE $A_4$

Two-stage treatment:

The following composition is applied to clean damp hair:

| | |
| --- | --- |
| Cationic silicone emulsion sold by Dow Corning under the name DC929 | 0.5 g |

-continued

| | |
|---|---|
| Water q.s. | 100 g |

After an interval of a few minutes, the following composition is applied:

| | |
|---|---|
| Mixture of compounds of Example 2 | 0.5 g |
| Water q.s. | 100 g | fter an interval of a few minutes, the hair is rinsed and dried. The hair is easy to shape and has a good hold.

We claim:

1. A product comprising a compound of formula (I):

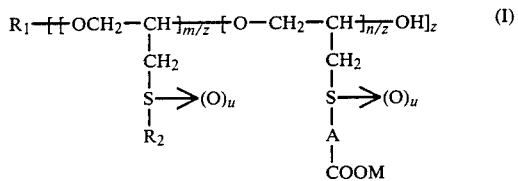

in which
- $R_1$ denotes an aromatic or alkylaromatic radical of 6 to 18 carbon atoms or an aromaticoxyethyl, alkylaromatic-oxyethyl, aromaticpolyoxyethyl or alkylaromaticpolyoxyethyl radical, of valency z, the alkyl part having from 1 to 12 carbon atoms and the oxyethyl part containing from 1 to 20 ethylene oxide groups;
- z denotes an integer from 1 to 6;
- $R_2$ denotes an aliphatic radical of 4 to 18 carbon atoms;
- A denotes an alkylene radical of 1 to 3 carbon atoms;
- M denotes a hydrogen atom, an alkali metal or alkaline earth metal atom, an ammonium ion or a substituted ammonium ion;
- m denotes an integer or decimal number from 1 to 10;
- n denotes an integer or decimal number from 1 to 20; and
- u denotes zero or 1.

2. A product according to claim 1 in which $R_1$ is derived by removing the —OH hydrogen atom from a monohydric or polyhydric phenol radical of benzene, naphthalene, biphenyl, diphenylmethane or 2,2-diphenylpropane, which is unsubstituted or substituted by one or more alkyl radicals of 1 to 12 carbon atoms, or an aromaticoxyethyl, alkylaromaticoxyethyl, aromaticpolyoxyethyl or alkylaromaticpolyoxyethyl radical, the alkyl part having from 1 to 12 carbon atoms and the oxyethyl part containing from 1 to 20 ethylene oxide groups.

3. A cosmetic composition which contains a product as claimed in claim 1 and a carrier.

4. A composition according to claim 3 which contains from 0.3 to 80% by weight of the product as claimed in claim 1 relative to the total weight of the composition.

5. A composition according to claim 3 presented in the form of an aqueous or aqueous-alcoholic solution or dispersion, a paste, a gel, a cream, an emulsion, a solid or an aerosol.

6. A composition according to claim 3 which contains at least one adjuvant selected from the group comprising anionic, cationic, zwitterionic, amphoteric and non-ionic surface-active agents, anionic, cationic, zwitterionic and non-ionic resins, proteins, foam synergistic agents, thickeners, opacifiers, super-fatting agents, preservatives, pigments, dyestuffs, sun filters, reducing agents, oxidizing agents, solvents, propellants and electrolytes.

7. A hair treatment process, wherein a composition as claimed in claim 3 is applied to the hair and, optionally, the hair is rinsed.

8. A two-stage hair treatment process, wherein, in a first stage, a cationic composition containing a surface-active agent or a cationic polymer is applied to damp hair and, after a few minutes of contact, a composition as claimed in claim 3 is applied, after which the hair is optionally rinsed and/or dried.

* * * * *